(12) United States Patent
Sharma et al.

(10) Patent No.: US 8,546,448 B2
(45) Date of Patent: Oct. 1, 2013

(54) 3-SUBSTITUTED COMPOUNDS FOR REDUCING URIC ACID

(75) Inventors: Shalini Sharma, Gaithersburg, MD (US); James Dennen O'Neil, Frederick, MD (US); Rita O'Neil, legal representative, Frederick, MD (US); Reid W. von Borstel, Potomac, MD (US); Ramchandran Arudchandran, Germantown, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 13/501,338

(22) PCT Filed: Sep. 15, 2011

(86) PCT No.: PCT/US2011/051781
§ 371 (c)(1),
(2), (4) Date: Apr. 11, 2012

(87) PCT Pub. No.: WO2012/037362
PCT Pub. Date: Mar. 22, 2012

(65) Prior Publication Data
US 2012/0201803 A1 Aug. 9, 2012

Related U.S. Application Data

(60) Provisional application No. 61/251,098, filed on Oct. 13, 2009.

(51) Int. Cl.
*A61K 31/275* (2006.01)
*A61K 31/195* (2006.01)
*C07D 257/00* (2006.01)
*C07C 229/00* (2006.01)

(52) U.S. Cl.
USPC ........... 514/522; 514/533; 514/564; 548/252; 548/253; 562/451

(58) Field of Classification Search
USPC ................. 514/522, 533, 564; 548/252, 253; 562/451; 558/416
See application file for complete search history.

(56) References Cited

U.S. PATENT DOCUMENTS

| 4,024,253 | A |   | 5/1977  | Umezawa et al. |         |
|-----------|---|---|---------|----------------|---------|
| 5,064,830 | A | * | 11/1991 | Going          | 514/248 |
| 5,274,000 | A | * | 12/1993 | Tomiyama et al.| 514/465 |
| 2004/0019208 | A1 |   | 1/2004 | Nivorozhkin et al. |     |
| 2008/0015209 | A1 |   | 1/2008 | Sharma et al. |         |
| 2008/0015254 | A1 |   | 1/2008 | Hodge et al.  |         |
| 2011/0014176 | A1 | * | 1/2011 | O'Neil et al. | 424/94.4 |
| 2011/0082209 | A1 | * | 4/2011 | Keel et al.   | 514/563 |
| 2011/0086921 | A1 | * | 4/2011 | Vallance      | 514/570 |
| 2011/0206653 | A1 | * | 8/2011 | O'Neil et al. | 424/94.4 |

FOREIGN PATENT DOCUMENTS

WO 2009/134995 A3 11/2009
WO 2009/151695 A1 12/2009

* cited by examiner

*Primary Examiner* — Raymond Henley, III
(74) *Attorney, Agent, or Firm* — Lewis J. Kreisler (57) ABSTRACT

A process for forming a solid electrolytic capacitor and an electrolytic capacitor formed by the process. The process includes: providing an anode wherein the anode comprises a porous body and an anode wire extending from the porous body; applying a thin polymer layer onto the dielectric, and forming a dielectric on the porous body to form an anodized anode; applying a first slurry to the anodized anode to form a blocking layer wherein the first slurry comprises a first conducting polymer with an median particle size of at least 0.05 μm forming a layer of crosslinker on the blocking layer; and applying a layer of a second conducting polymer on the layer of crosslinker.

20 Claims, 2 Drawing Sheets

3-SUBSTITUTED COMPOUNDS FOR REDUCING URIC ACID

CROSS-REFERENCE TO RELATED APPLICATIONS

The present application claims priority to U.S. Provisional Patent Application No. 61/383,076 filed Sep. 15, 2010 which is incorporated herein by reference.

BACKGROUND

The present invention is related to an improved process for forming a capacitor and a capacitor formed thereby. More specifically, the present invention is related to the optimization of a polymer layer in a solid electrolytic capacitor for improved humidity performance.

Solid electrolytic capacitors with conductive polymers as the cathode material have been widely used in the electronics industry due to their advantageously low equivalent series resistance (ESR) and their non-burning/non-ignition failure mode. The typical compositions and properties of polymer slurry are illustrated in U.S. Pat. No. 5,300,575 which is incorporated herein by reference.

U.S. Pat. No. 6,391,379, which is incorporated herein by reference, discloses a process that involves multiple coating-drying process steps, thereby significantly simplifying the process of polymer dispersion.

U.S. Pat. No. 7,563,290, which is incorporated herein by reference, describes the slurry/dispersion process. The resulted capacitors show excellent high voltage performances, reduced DC leakage (DCL) and improved long term reliability.

It is highly desirable that the capacitor devices are of high reliability and that they can withstand stressful environments. Therefore, the integrity of the anodes and the robustness of conductive polymer cathode are essential for high quality capacitor products. However, it is a challenge to form a conductive polymer coating on the anodes that is defect-free, and which is capable of withstanding thermal mechanical stress during anode resin encapsulation and surface-mounting. The improper application of polymer slurry often leads to the formation of cracks and delaminating of the polymer coating thus formed.

In a manufacturing process to produce conductive polymer based valve metal capacitors the valve metal powder, such as tantalum, is mechanically pressed into anodes that are subsequently sintered to form porous bodies. The anodes are anodized to a pre-determined voltage in a liquid electrolyte to form a dielectric layer onto which a cathode layer of conductive polymer is subsequently formed via an in situ polymerization process comprising multi-cycle oxidizer/monomer coatings and polymerization reactions. The anodes are then coated with graphite and Ag followed by assembling and molding into a finished device.

A particular concern is the formation of adequate polymer coatings on edges and corners. In order to achieve good quality polymer coating on anodes, especially on the corners and edges, many types of chemical compounds are used for either forming a pre-coating on the anode or which are added to the polymer slurry. U.S. Pat. No. 7,658,986, which is incorporated herein by reference, describes the difficulty in coating the edges and corners of the anode with polymer slurry. These materials tend to pull away from the corners and edges due to surface energy effects. The resulting thin coverage at corners and edges leads to poor reliability of the device.

In general, the formation of coatings on edges is well understood. In fact, the magnitude of the force pulling the liquid away from the edge is given by the Young and Laplace:

$\Delta p = \gamma / r$ wherein:

$\Delta p$ = the pressure difference causing the liquid or slurry to recede from an edge;
$\gamma$ = the surface tension of the liquid or slurry; and
$r$ = the radius of curvature of the edge.

Figure 1:
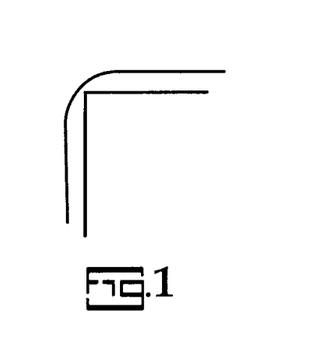
FIG. 1 illustrates the problem associated with poor edge and corner coverage.

This effect of liquid distribution on corners and edges of an anode is illustrated in FIG. 1.

One approach to mitigating poor coverage of the anode corners and edges has been to alter the design of the anode as disclosed in U.S. Pat. Nos. 7,658,986, D616,388, D599,309, and D586,767 each of which is incorporated herein by reference. While changes in the anode design are beneficial in some regards the effect of poor coverage is still present even with anode designs which facilitate corner and edge coverage by polymer slurry as the primary cathode layer.

Another approach for improving coverage of the corners and edges is provided in International Application WO2010089111A1, which is incorporated herein by reference, which describes a group of chemical compounds called crosslinkers, which are mostly multi-cationic salts or amines, such as an exemplary material decanediamine toluenesulfonate. International Application WO2010089111A1 teaches the application of a solution of the crosslinker on the anodes prior to the application of polymer slurry to achieve good polymer coverage on corners and edges of the anodes. The effectiveness of the crosslinker is attributed to the crosslinking ability of multi-cationic salts or amines to the slurry/dispersion particles. While crosslinkers are advantageous for improving the coating coverage on corners and edges of the anodes, the addition of these crosslinkers, which are mostly ionic in nature, has the unintended consequences of degrading the humidity performance of finished product.

Removing the crosslinker has not been considered feasible. It is widely accepted that the polymer layer is not to be washed due to expected disruption in the bonding between the polymer and the underlying surface, furthermore, it is widely known that the polymer layers are susceptible to swelling and dedoping resulting in an increase in ESR. U.S. Pat. No. 6,391,379 for example, which is incorporated herein by reference, teaches redissolution of the polymer layer. U.S. Pat. No. 6,987,663 and U.S. Pat. No. 7,377,947, both of which are incorporated herein by reference, teach that contacting the polymer layer with an aqueous electrolyte may cause the polymer slurry layer to detach from the anode body. Therefore, one of skill in the art would be expected to avoid washing the polymer layer.

There has been a long standing challenge to make a capacitor with low ESR and adequate humidity performance.

SUMMARY OF THE INVENTION

It is an object of the invention to provide polymer cathode based capacitors with excellent humidity performance and excellent electrical properties.

It is another object of the invention to provide a process that can produce polymer cathode based capacitors with excellent humidity performance and excellent electrical properties.

It is another object of the invention to provide a method for effectively reducing or controlling the residual ionic content of polymer cathode based capacitors.

These and other advantages, as will be realized, are provided in a process for forming a solid electrolytic capacitor and an electrolytic capacitor formed by the process. The process includes:
providing an anode wherein the anode comprises a porous body and an anode wire extending from the porous body;
forming a dielectric on the porous body to form an anodized anode; coating the anodes with a thin layer conductive polymer,
applying a first slurry to the anodized anode to form a blocking layer wherein the first slurry comprises a first conducting polymer slurry with a median particle size of at least 0.05 µm
forming a layer of crosslinker on the blocking layer; and
applying a layer of a second conducting polymer slurry on the layer of crosslinker.

Yet another embodiment is provided in a process for forming a solid electrolytic capacitor and a capacitor formed by the process. The process includes:
providing an anode wherein the anode comprises a porous body and an anode wire extending from the porous body;
forming a dielectric on the porous body to form an anodized anode; coating the anodes with a thin layer conductive polymer,
applying a first conducting polymer slurry layer on the anodized anode wherein the first conducting polymer slurry has a median particle size of at least 0.05 µm forming a layer of crosslinker on the conducting polymer layer; and
applying a layer of a second conducting polymer slurry on the layer of crosslinker;
wherein after applying the second conducting polymer slurry the crosslinker concentration is no more than 3500 µg per gram of a combination consisting of the anode, the dielectric, and all conducting polymer.

Yet another embodiment is provided in a solid electrolytic capacitor. The solid electrolytic capacitor has a porous body with planar faces and corners and a dielectric on the porous body. A conducting polymer is on the dielectric wherein the conducting polymer has a thickness measured from an apex of the corners of at least 1 µm (1 µm=1×10$^{-6}$ m) to no more than 15 µm. The capacitor has no more than 3500 µg crosslinker per gram of a combination consisting of the anode, the dielectric, and all conducting polymer.

Yet another embodiment is provided in a process for forming a solid electrolytic capacitor and a solid electrolytic capacitor prepared by the process. The process includes:
providing an anode wherein the anode comprises a porous body and an anode wire extending from the porous body;
forming a dielectric on the porous body to form an anodized anode; coating the anodes with a thin layer conductive polymer,
forming a layer of crosslinker;
applying a layer of conducting polymer; and
washing to remove excess crosslinker.

DETAILED DESCRIPTION

Provided herein is an improved capacitor and a method for making the improved capacitor. More particularly, provided herein is a method that allows the production of capacitors with improved consistency which are less susceptible to failure in humid conditions.

A family of crosslinking compounds is used to achieve improved polymer coverage of the anodes, especially on the corners and edges. It is believed that these crosslinkers, once pre-coated onto the dielectric of the anode, may interact or cross-link with polymer slurry particles when subsequently exposed to the slurry dispersion thereby forming a uniform coating layer over the entire dielectric surface of the anode including the corners and edges. The crosslinkers, which are primarily ionic, tend to be incorporated into the polymer coating. The crosslinkers achieve improved polymer coverage on the dielectric of the anodes, especially on the corners and on edges.

Through diligent research, it has been realized that the use of these crosslinking compounds for improved polymer coverage results in products with good initial performance characteristics yet long term reliability of the product is adversely affected, especially, when operating in humid environments. The long term reliability has thwarted the use of crosslinkers in many applications.

Solid electrolytic capacitors generally comprise a porous metal anode, an oxide layer on the anode, typically an oxide of the anode metal, and an electrically conductive solid cathode, such as manganese dioxide or an intrinsically conductive polymer, incorporated into the pores and onto the dielectric. Additional layers, such as silver and carbon layers, are then added to aid in contact formation.

The solid electrolytic capacitors typically incorporate valve metals or conductive oxides of valve metals with tantalum, aluminum, niobium and niobium oxide being mentioned as particularly preferred. An advantage of the high surface area is that a very high capacitance density can be achieved.

Conjugated polymers are particularly suitable for use as the electrically conductive solid cathode with polyaniline, polypyrroles and polythiophenes being most preferred. A particularly preferred polymer for use as a cathode is polythiophene. The polymer precursors are polymerized to form the conductive layer which functions as the cathode of the capacitor. The polymer precursors are preferably polymerized by either electrochemical or chemical polymerization techniques with oxidative chemical polymerization being most preferred. In one embodiment, the conductive layer is formed by dipping the anodized substrate first in a solution of an oxidizing agent such as, but not necessarily limited to iron (III) p-toluenesulfonate. After a drying step, the anode bodies are then immersed in a solution comprising monomer and oligomer of the conductive polymer and solvents.

It is preferred to include a dopant in the polymer as known in the art. The dopant can be coated separately or included in the polymer slurry or monomer solution. A particularly preferred dopant is the sodium salt of polystyrenesulfonate (PSS).

In one embodiment a polymer precursor comprising a monomer and conjugated oligomer is used. The monomer preferably represents about 75-99.9 wt % of the polymer precursors and the conjugated oligomer preferably represents about 0.1-25 wt % of the polymer precursors. More preferably the monomer represents about 90-99.9 wt % of the polymer precursors and the conjugated oligomer represents about 0.1-10 wt % of the polymer precursors. Even more preferably the monomer represents about 95-99.5 wt % of the polymer precursors and the conjugated oligomer represents about 0.5-5 wt % of the polymer precursors. The preferred monomer is a compound of Formula I and the preferred oligomer is a compound of Formula II.

The conducting polymer is preferably an intrinsically conducting polymer comprising repeating units of a monomer of Formula I and optionally an oligomer Formula II:

FORMULA I

FORMULA II $R^1$ and $R^2$ of Formula I and $R^4$-$R^9$ of Formula II are chosen to prohibit polymerization at the β-site of the ring. It is most preferred that only α-site polymerization be allowed to proceed. Therefore, it is preferred that $R^1$ and $R^2$ are not hydrogen. More preferably $R^1$, $R^2$, $R^4$, $R^5$, $R^6$, $R^7$, $R^8$ and $R^9$ are α-directors. Therefore, ether linkages are preferable over alkyl linkages. It is most preferred that the groups are small to avoid steric interferences. For these reasons $R^1$ and $R^2$, $R^4$ and $R^5$, $R^6$ and $R^7$ or $R^8$ and $R^9$ each taken together as —O—$(CH_2)_2$—O— is most preferred.

In Formula II n is an integer selected from 0-3.

In Formulas I and II, X and Y independently are S, Se or N. Most preferably X and Y are S.

$R^1$, $R^2$, $R^4$, $R^5$, $R^6$, $R^7$, $R^8$ and $R^9$ independently represent linear or branched $C_1$-$C_{16}$ alkyl or $C_1$-$C_{18}$ alkoxyalkyl; or are $C_3$-$C_8$ cycloalkyl, phenyl or benzyl which are unsubstituted or substituted by $C_1$-$C_6$ alkyl, $C_1$-$C_6$ alkoxy, halogen or $OR^3$; or $R^1$ and $R^2$, $R^4$ and $R^5$, $R^6$ and $R^7$ or $R^8$ and $R^9$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements. $R^3$ preferably represents hydrogen, linear or branched $C_1$-$C_{16}$ alkyl or $C_1$-$C_{18}$ alkoxyalkyl; or are $C_3$-$C_8$ cycloalkyl, phenyl or benzyl which are unsubstituted or substituted by $C_1$-$C_6$ alkyl.

More preferably $R^1$, $R^2$, $R^4$, $R^5$, $R^6$, $R^7$, $R^8$ and $R^9$ independently of one another, represent —$CH_3$, —$CH_2CH_3$, —$OCH_3$; —$OCH_2CH_3$ or most preferably $R^1$ and $R^2$, $R^4$ and $R^5$, $R^6$ and $R^7$ or $R^8$ and $R^9$ are taken together to represent —$OCH_2CH_2O$— wherein the hydrogen can be replaced with a solubilizing group, a halide or an alkyl.

Terms and chemical formulas used herein to refer to alkyl or aryl moieties refer to either the substituted or unsubstituted moiety unless specifically stated otherwise. A solvent is defined as a single solvent or a mixture of solvents.

The synthesis of conjugated dimers and trimers is well known in the literature. For example, the dimer of 3,4-ethylenedioxythiophene can be made through Ulmann coupling of the monomers with alkyl lithium and cupric chloride [J. Kagan and S. K. Arora, Heterocycles, 20 (1983) 1937].

Conjugated and non-conjugated dimers can be distinguished by Fourier transform infrared (FT-IR) spectroscopy, and by nuclear magnetic resonance (NMR). The content of the conjugated as well as non-conjugated dimers in the monomer can be measured by gas chromatograph (GC).

The polymer layer can be formed by in-situ polymerization on the surface or by applying a slurry of polymer onto the dielectric coated such as by dipping or spraying. These techniques are described in the literature and are widely understood and will not be further explained herein. Achieving adequate coverage of the edges and corners is difficult as set forth above. The choice of method for forming the polymer layer is selected based, in part, on the location of the layer being formed. It is widely known that a conductive polymer layer is typically formed by multiple applications of thinner layers each of which may be formed by either in-situ polymerization or by slurry dipping.

It is preferable to apply the solution of dispersion comprising the conductive polymer or crosslinker at a pH of no more than 10 and more preferably no more than 8 with below 7 being more preferred and below 6 being especially preferred as measured at 25° C.

In one embodiment crosslinking compounds comprise at least one diamine, triamine, oligoamine or polymeric amine or a derivative thereof, at least one cation and at least one amine group, or at least one polyvalent cation or, forms at least one polyvalent cation after application of the conductive polymer. Oligoamines are defined as those amines which contain at least four amines such as tetramers, pentamers, hexamers, heptamers, octamers, nonamers, decamers, undecamers or dodecamers.

In one embodiment the polyvalent cation of the crosslinking compound is preferably a metal polyvalent cation, a compound with at least two phosphonium groups, a compound with at least one phosphonium group and at least one amine group or a compound with at least two sulfonium groups.

Polyvalent metal cations include salts or compounds of Mg, Al, Ca, Fe, Cr, Mn, Ba, Ti, Co, Ni, Cu, Ru, Ce, Zn or alloys thereof. Particularly preferred examples are selected from $MgBr_2$, $MgCl_2$, $MgSO_4$, $ZnBr_2$, $ZnCl_2$, $ZnSO_4$, $AlCl_3$, $Al_2(SO_4)_3$, $CuCl_2$, $CuSO_4$, $TiOSO_4$, $FeCl_2$, $FeCl_3$, $FeSO_4$ and $Fe_2(SO_4)$.

Triphenylphosphonium compounds are mentioned as suitable compounds with at least two phosphonium groups such as (2-dimethylaminoethyl) triphenylphosphonium bromide or p-xylyenebis(triphenylphosphonium bromide).

A representative example of a compound with a phosphonium group and an amine group is (2-dimethyl-aminoethyl) triphenylphosphonium bromide or derivatives thereof.

Triarylsulfonium salts such as:

are representative of compounds with at least two sulfonium groups.

Representative amine based crosslinkers include aliphatic amines such aliphatic α,ω-diamines, such as 1,4-diaminocyclohexane or 1,4-bis(aminomethyl)cyclohexane; ethylenediamine; 1,6-hexanediamine; 1,7-heptadiamine; 1,8-octanediamine 1,9-nonanediamine; 1,10-decanediamine; 1,12-dodecanediamine, N,N-dimethylethylenediamine; N,N,N'N'-tetramethylethylenediamine; N,N,N'N'-tetramethyl-1,4-butanediamine; N,N,N,N'N'N'-hexamethylhexamethylene-diammonium dibromide;

piperazine; 1,4-diazabicyclo[2.2.2]octane; N,N,N'N'-tetrakis (2-hydroxypropyl)ethylenediamine; N-[3-trimethoxysilyl) propyl]ethylenediamine; 1,4-bis(3-aminopropyl)piperazine; N,N'diacetyl-1,6-hexanediamine; N,N,N',N'-tetraacetylethylene diamine; 1,4-diformylpiperazines; N,N'-ethylenebis (stearamide); 1,4-bis(3-aminopropyl)piperazine; N-(6-aminohexyl)-1,6-diaminohexane; N-(3-aminopropyl)-1,4-diaminobutane; 3-[2-(2-aminoethylamino)ethylamino] propyltrimethoxysilane; 4,4'-methylenebis(N,N-diglycidylaniline); o-phenylene-diamine; m-phenylenediamine; p-phenylenediamine; 1,5-diaminonaphthalene; 1,8-diaminonaphthalene; 2,3-diaminonaphthalene; 3-aminophenyl sulfone; 4-aminophenyl sulfone; 4-aminophenyl ether; 3,3'-diaminobenzidine; 2-(4-aminophenyl) ethylamine; 4,4'-methylenedianiline; 2,6-diaminotoluene; N,N,N'N'-tetramethyl-p-phenylenediamine; 4,4'-bis(diethylaminobenzophenone; 4,4'-bis(dimethylamino)benzhydrol; 3,3',5,5'-tetramethylbenzidine; Auramine O; Rubine S; m-xylenediamine; phthalein; Brilliant Blue G; folic acid; 4,4', 4"-methylidinetris(N,N-dimethylaniline); citrulline; arginine; glutamine; lysine; asparagine; histidine; tryptophan; poly(propylene glycol)-bis(2-aminopropyl) ether; polyethyleneimine; poly(allylamine); ethoxylated polyethyleneimine;

Particularly preferred crosslinkers are aliphatic α,ω-diamines and more particularly preferred crosslinkers are linear aliphatic α,ω-diamines with even more preferred crosslinkers comprises at least one material selected from the group consisting of diaminooctane, diaminononane, diaminodecane, diaminoundecane or derivatives thereof.

As a polyvalent cation the crosslinking may be formed after application of the solution of dispersion, by reacting with the solution or dispersion, or by reacting with further additives to the solution or dispersion. By way of non-limiting example, the crosslinker can comprise metal applied to the capacitor body by a known method, such as vapor deposition, sputtering or sublimation, and when contacted with a solution or dispersion with a pH of less than 7 the corresponding metal cations, such as $Ca^{2+}$, may be formed thereby improving the corner and edge coverage of the capacitor body by the conductive polymer.

The crosslinker is preferably applied as a solution by dipping or by spraying. The crosslinker solution preferably comprises at least 4 wt % to no more than 15 wt % of crosslinker. More preferably the crosslinker solution preferably comprises at least 6 wt % to no more than 10 wt % of crosslinker and even more preferably the crosslinker solution preferably comprises at least 7 wt % to no more than 9 wt % of crosslinker at room temperature.

The pH of the amine based crosslinkers can be adjusted by adding organic or inorganic acids, diacids, triacids, polymeric acids, etc. Particularly suitable acids include sulfuric acid, phosphoric acid, nitric acid, carboxylic acids or sulfonic acids. Acids which are particularly suitable for demonstration of the invention include $C_1$-$C_{20}$-alkanesulfonic acids such as methanesulfonic acid, ethanesulfonic acid, propanesulfonic acid, butanesulfonic acid or higher sulfonic acids such as dodecanesulfonic acid. Aliphatic perfluorosulfonic acids mentioned include trifluoromethanesulfonic acid, perfluorobutanesulfonic acid, perfluorooctanesulfonic acid, perfluorobutanesulfonic acid or aliphatic $C_1$-$C_{20}$-carboxylic acids such as 2-ethylhexylcarboxylic acid, or aliphatic perfluorocarboxylic acids such as trifluoroacetic acid or perfluorooctanoic acid. Aromatic sulfonic acids or aromatic sulfonic acids substituted such as with $C_1$-$C_{20}$-alkyl groups are mentioned such as benzenesulfonic acid, o-toluenesulfonic acid, p-toluenesulfonic acid or dodecylbenzenesulfonic acid as are cycloalkanesulfonic acids such as camphorsulfonic acid. Disulfonic acids, trisulfonic acids, dicarboxylic acids, tricarboxylic acids, polyacrylic acids, polymethacrylic acids, polymaleic acids and polymeric sulfonic acids are suitable for demonstration of the teachings including polystyrenesulfonic acids, polyvinylsulfonic acids and copolymers thereof.

The crosslinker can be applied to the corners or edges and it is preferable that, at least, the edges and corners have crosslinker. It is more practical to apply crosslinker to the entire outer surface of the capacitor body. It is preferable to at least partially remove any solvent or dispersant with thermal removal at temperatures of 15° C. to 200° C., and more preferably 50° C. to 150° C.

A conductive polymer slurry is applied onto the dried crosslinking material to form a layer that covers the edges and corners of the anodes. The polymer slurry preferably has less than 5000 mg of metal/kg of slurry, more preferably less than 1000 mg of metal/kg of slurry and most preferably less than mg of metal/kg of slurry with specific metals to be maintained below this level to preferably include Na, K, Mg, Al, Ca, Fe, Cr, Mn, Co, Ni, Cu, Ru, Ce and Zn since they can interfere with accurate control of the crosslinker.

To maintain the optimal performance of the dispersion and polymer precursor solution or polymer slurry solution it is preferable to utilize ion exchangers either continuously or in phases to remove contaminants.

The sequence of applying a crosslinking material followed by applying a conductive polymer layer is repeated many times until the desired layer thickness is reached. Without limit thereto 2-10 cycles of crosslinking material and conductive polymer layer application is suitable for demonstration of the invention. Each application of a dried crosslinking material may be with a unique crosslinker material and/or concentration of crosslinking material or the applications may be with an identical or similar material. Similarly, each application of the conductive polymer may use a unique composition and a unique solution or an identical or similar material may be used for the various dipping steps.

After the desired numbers of polymer layers are formed, or the desired thickness is achieved, it is preferable to apply layers which facilitate adhesion to a lead frame. Conductive carbon layers followed by conductive metal layers, particularly noble metal or semi-noble metal layers, are formed on the conductive polymer. The capacitor is finished after attaching to external leads, encapsulation, testing, packaging and the like.

Figure 2:
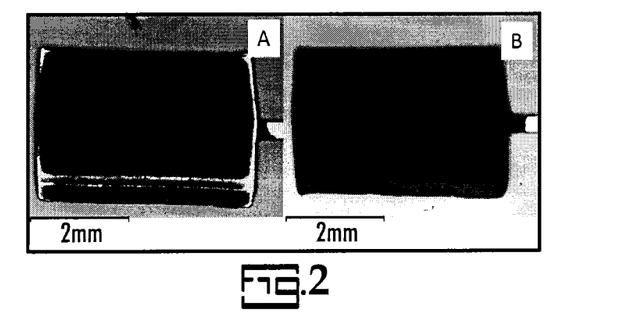
FIG. 2 is an illustration comparing polymer coverage with crosslinker (A) and without crosslinker (B).

FIG. 2 illustrates the difference in the polymer coverage on the dielectric of the anodes with and without the use of the crosslinker. It is clear that the crosslinker is effective for improving polymer coverage on the edges and corners of the anode. The average layer thickness was measured and is shown in Table 1. A layer thickness of 1-15 μm, preferably 2-15 μm, more preferably 5-15 μm and most preferably 6-15 μm on corners and edges of anode is preferred for highly reliable capacitors that are expected to withstand the extreme stress of solder reflow and harsh environments. It is preferable that the ratio of thickness of the polymer on the face to the thickness of the polymer on at least one corner, measured perpendicular to the face or apex of the corner, is no more than 20:1 and more preferably no more than 10:1. The anodes shown as A in FIG. 2 will fail under those conditions.

TABLE 1

Impact of "crosslinker" on polymer coverage

| | Corner Layer Thickness, μm |
|---|---|
| No crosslinker | 0.9 |
| With crosslinker | 12.3 |

Based on the surprising results detailed herein, the effectiveness of crosslinkers is related to its quantity in or on the surface being polymer coated with higher solution concentrations of crosslinker yielding better polymer coverage on corners and edges of anodes. However, when the concentration approaches saturation point, the solution becomes unstable and precipitates. Elevated temperature allows the use of higher concentration solutions. A solution of at least 4-15 wt %, preferably 6-15 wt %, more preferably 7-15 wt % and most preferably 8-15 wt % measured at 35-50° C. is desirable for effective processing.

Unfortunately, crosslinkers render the eventual capacitor more susceptible to unacceptable performance characteristics when subjected to humid conditions. Therefore, the effective use of crosslinkers has been thwarted due to a lack of suitability in capacitors which may be subjected to humid conditions. The use of these crosslinkers for improving polymer coverage results in products with good initial performance characteristics, however, long term reliability of the product is adversely affected, especially when operating in humid environments. Since high humidity is a common environmental condition for capacitors, crosslinkers have not been exploited to their full potential.

While not limited to any theory it is hypothesized that the crosslinkers interact with and remain in the conductive polymer layers due to their hydroscopic nature and when the capacitor operates in a humid environment the crosslinker leaches out the conductive polymer layers and towards or into the encapsulant. Once the capacitor encapsulant becomes saturated a parasitic electrolytic cell is formed inside the capacitor casing. Applying a voltage over such a capacitor may initiate many reactions, including electrolysis, migration wherein charged particles move under electrical field, and corrosion which degrades the dielectric, the cathode, the graphite/Ag layer, and/or their interfacial layers which leads to higher DC leakage, higher ESR, and eventually complete electrical failure.

It is clearly a challenge to effectively use these crosslinkers to improve polymer coverage without causing performance degradation. In direct contrast to the expectations in the art superior product performance can be achieved by controlling the crosslinker content of the anode below 4000 μg/g of anode mass, based on the anode, dielectric and polymer coating but excluding Ag and any subsequent layer added. More preferably the crosslinker content is maintained below 3000 μg/g of anode mass and most preferably below 1500 μg/g of anode mass.

Figure 3:
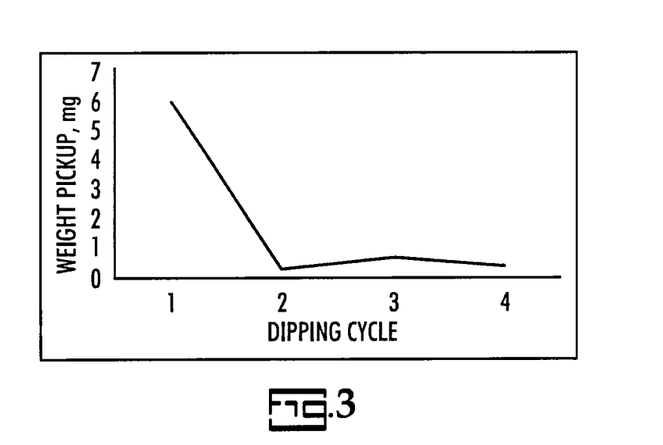
FIG. 3 graphically illustrates the weight pickup of crosslinker as a function of dipping cycles.

The method of controlling crosslinker concentration below the preferred level in a capacitor is done by limiting the amount used or by removing the excess. In one embodiment the amount of crosslinker applied during the coating process is limited. Surprisingly in a process utilizing a multi-cycle sequential dipping of crosslinker and polymer slurry, the most weight pick up of the crosslinker occurs during the $1^{st}$ cycle, as shown in FIG. 3, wherein grams of crosslinker in the anode as a function of dip cycles is plotted. While not limited to any theory, the high weight pick up is attributed to the fact that the anodes, without any external polymer slurry coating, are porous and absorb crosslinker solution into the interstitial portion of the anode. This interstitial absorbed crosslinker is not effective at crosslinking the subsequently coated polymeric cathode layers yet it is sufficiently mobile in humid conditions and can contribute to inferior performance. In contrast to the teachings in the art, it is advantageous to apply a polymer coating on anodes prior to coating with crosslinker to block the access of crosslinkers to the pores, thereby forcing crosslinkers to form a thin surface layer for higher process efficiency.

A blocking layer of conductive polymer is preferably applied on the dielectric prior to applying the crosslinking compound. This can be achieved by applying a coating of polymer slurry in which the median particle size of the polymer particles should be at least 0.05 μm, and more preferably 0.065 μm, measured by ultracentrifuge, or similar technique in order to effectively blocking the crosslinker from entering the interstitial spaces of the porous anode.

After application of the blocking layer the solution or dispersion containing the crosslinker and the solution or dispersion containing the polymer precursors or polymer can be alternately applied to obtain the desired thickness. The number of cycles is preferably less than 10, most preferably between 2 and 6.

Polymer layers applied prior to, or after, the blocking layer can be applied by in-situ polymerization or by applying a slurry. If slurry is utilized for other than the blocking layer the particle size of polymer particles is not particularly limited herein even though it may be preferred, for manufacturing simplicity, to use the same polymer slurry for each layer.

An embodiment of the invention will be described with reference to FIG. 4 wherein a process of the invention is represented in the form of a flow chart.

Figure 4:
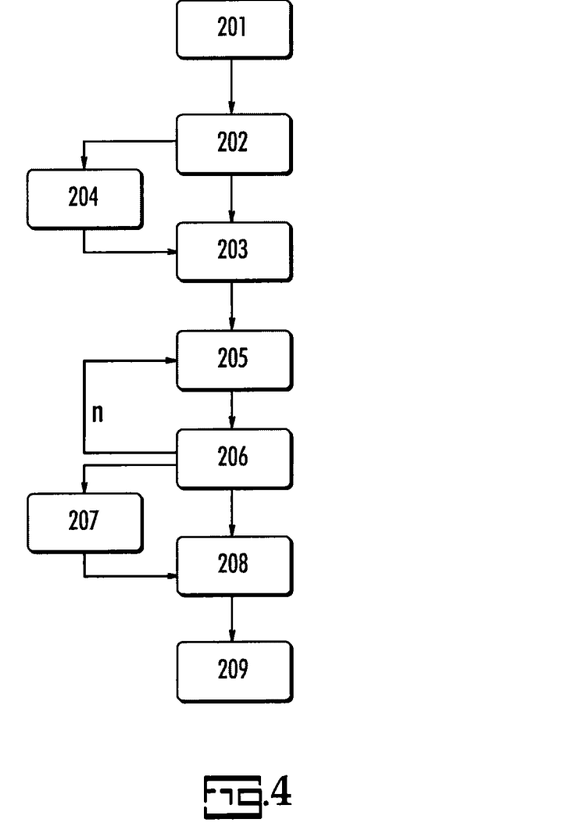
FIG. 4 is a flow chart representation of an embodiment of the invention.

In FIG. 4, a porous anode is provided at 201. The anode has a porosity defined by median pore size. While not limited thereto the median pore size, is typically ranging from 0.01

μm to 10 μm. The porous anode is typically formed by pressing a powder of, preferably, a valve metal, or by etching a sheet of, preferably, a valve metal. A dielectric is formed on the anode at 202 to form an anodized anode followed by coating a thin conductive polymer layer. The dielectric is preferably an oxide of the anode material due to the manufacturing simplicities provided thereby, however, the dielectric can be formed on the surface of the anode by any method known in the art.

A blocking layer is formed at 203. The blocking layer is formed by dipping the anodized anode into a polymer slurry wherein the polymer particles of the slurry are of a sufficient size to not enter the pores of the anodized anode. In practice a median particle size of at least 0.05 μm measured by ultracentrifuge, or similar technique is suitable for demonstration of the invention. Smaller polymer particles will make the blocking layer less effective thereby allowing crosslinking compounds to enter the interstitial portion of the anode. It is hypothesized that the crosslinking compounds in the interstitial portion of the anode do not participate effectively in the crosslinking and are susceptible to migration outward under some conditions, such as in the presence of high humidity, which is detrimental to the performance of the eventual capacitor.

In an alternative embodiment a pre-layer of conductive polymer can be applied at 204 wherein the pre-layer is applied prior to the application of a blocking layer. The pre-layer can be applied by dipping the anodized anode in a slurry or by in-situ polymerization. It is most preferred to form a thin layer of conductive polymer by in-situ polymerization.

After the blocking layer is applied a layer of dried crosslinking material is formed at 205. The layer of dried crosslinking material is formed by applying the anodized anode comprising at least a blocking layer thereon into a solution of crosslinking material. The solvent is then removed providing a coating of dried crosslinking material.

A conductive polymer layer is formed on the dried crosslinking material at 206. The conductive polymer layer may be formed by in-situ polymerization or by dipping in a polymer slurry. It is preferable to apply the conductive polymer layer by dipping in a polymer slurry. The particle size used for the polymer slurry is not particularly limiting for formation of the conductive polymer layer. In one embodiment the polymer slurry is the same as that used for the blocking layer since this simplifies the manufacturing process and the number of materials handled during manufacturing.

The sequence of applying a crosslinking material followed by applying a conductive polymer layer is repeated "n" times until the desired layer thickness is reached. Without limit thereto 2-10 cycles of crosslinking material and conductive polymer layer application is suitable for demonstration of the invention. Each application of a dried crosslinking material may be with a unique crosslinker material and/or concentration of crosslinking material or the applications may be with an identical or similar material. Similarly, each application of the conductive polymer may use a unique composition and a unique solution or an identical or similar material may be used for the various dipping steps.

In one embodiment the polymer layers are washed at 207 to remove any crosslinking material which is not incorporated into a crosslinked bond. Washing of the polymer is contrary to the teachings in the art as described herein yet with the incorporation of the blocking layer a washing step can be incorporated without detriment to the eventual capacitor.

After the desired number of polymer layers are formed, or the desired thickness is achieved, it is preferable to apply layers which facilitate adhesion to a lead frame. Conductive carbon layers followed by conductive metal layers, particularly noble metal layers, are formed on the conductive polymer at 208. The capacitor is finished at 209 which may include attachment to external leads, encapsulation, testing, packaging and the like.

To maintain the optimal performance of the dispersion and polymer precursor solution or polymer slurry solution it is preferable to utilize ion exchangers either continuously or in phases to remove contaminants. For example, dipping in the polymer slurry after dipping in the crosslinker solution will transfer some crosslinker to the slurry and vice versa.

In another embodiment the amount of crosslinker can be reduced by washing. Prolonged exposure of the polymer slurry layer to water tends to cause the layer to swell and de-dope resulting in a noticeable increase in ESR as shown in Table 2 wherein the crosslinker residue contents on the anode are presented after washing at different temperatures. In the samples reported in Table 2, the crosslinker was decanediamine toluenesulfonate. The advantages of a washing step are directly contrary to the teachings in the art as exemplified in U.S. Pat. No. 6,391,379 wherein the concern of redissolution of the polymer slurry layer when exposed to solvents is discussed. It is considered advantageous to avoid a reform process, in which contact with aqueous electrolyte may cause polymer layer to detach from the anode body, as disclosed in U.S. Pat. No. 6,987,663 which is incorporated by reference.

TABLE 2

Impact of water wash on ESR

|  | ESR (mOhm) |
|---|---|
| No wash | 30 |
| Washed | 62 |

Washing temperature is important since a high temperature which is too high tends to damage polymer coating integrity causing excessive layer swelling and blistering, while a temperature that is too low reduces the wash effectiveness. Table 3 lists the "Crosslinker" residue contents on the anode per anode mass after washing at different temperature. It is preferable to wash with water at the temperature of at least 5° C. to no more than 85° C. More preferably, the water temperature is at least 30° C. and even more preferably at least 50° C.

TABLE 3

Impact of washing temperature

| Wash Temp. ° C. | Residue, μg/g |
|---|---|
| 30 | 1418 |
| 65 | 177 |

In a particularly preferred embodiment a proper crosslinker concentration and slurry dipping procedure is combined with a post process wash. A polymer coating is first formed on the dielectric, preferably by dipping the anode with the dielectric thereon into a slurry of polymer. After polymer coating a coating of crosslinker is applied followed by an alternating application of polymer and crosslinker. At least once prior to completion of the polymer coating buildup the polymer is washed with dionized water as detailed further herein.

Throughout the specification listed ranges are intended to include all intermediate ranges with the same number of significant figures. A range of 5-11, for example, is meant to also specifically recite 6, 7, 8, 9 and 10. A range of 0.05 to 0.10, for example, is intended to specifically recite 0.06, 0.07, 0.08 and 0.09.

Comparative Example

A series of V case 15 μF tantalum anode with a size of 4.7×3.3×0.8 mm was anodized at 100V. A thin coating of polyethylenedioxythiophene polymer (PEDOT) was applied on the dielectric of the anodes via an in-situ chemical polymerization process to achieve full capacitance. The anodes were then coated with PEDOT slurry. The above processes were repeated 3 more times. The anodes were analyzed for their chemical compositions and tested after graphite and Ag coating. The composition and electrical properties of their molded devices are summarized in Table 4. Since no crosslinker was used in the sample preparation, the yield was very low and most parts became short-circuited.

Inventive Example 1

A series of V case 15 μF tantalum anodes with a size of 4.7×3.3×0.8 mm was anodized at 100V. A thin coating of conductive polymer (PEDOT) was applied onto the anodes via an in-situ chemical polymerization process. The anodes were first coated with a blocking layer by applying a PEDOT slurry coating in order to minimize the pick-up of crosslinker. The PEDOT slurry comprised polymer particles with a median particle size of at least 0.05 μm measured by ultracentrifuge, or similar technique. After drying alternating layers of decanediamine toluenesulfonate and slurry were applied and repeated 3 more times. Graphite and Ag coatings were applied and the samples were analyzed for their chemical compositions and encapsulated in a mold. The composition prior to encapsulation and electrical properties after molding are summarized in Table 4. Though yield was significantly improved due to the use of crosslinker, there were still a few failures in the humidity test due to relatively high crosslinker residue despite attempt to reduce it by applying a slurry coating in prior to crosslinker applications.

Inventive Example 2

A series of V case 15 μF tantalum anodes with a size of 4.7×3.3×0.8 mm was anodized at 100V. A thin coating of conductive polymer (PEDOT) was applied onto the anodes via an in-situ chemical polymerization process. A blocking layer was applied by applying a PEDOT slurry in order to minimize the pick-up of crosslinker. The PEDOT slurry comprised polymer particles with a median particle size of at least 0.05 μm measured by ultracentrifuge, or similar technique. After drying alternating layers of decanediamine toluenesulfonate and PEDOT slurry were applied and repeated 3 more times. The samples were washed in deionized water for 30 minutes at room temperature followed by drying. Graphite and Ag coatings were applied and the samples were tested for their chemical compositions. After encapsulation the electrical properties were tested. The composition prior to encapsulation is summarized in Table 4 and the electrical properties of the molded devices are summarized in Table 5. Good yield and humidity performances were achieved when the residue level of crosslinker was properly controlled.

TABLE 4

|  | Crosslinker μg/g | Crosslinker μM/g | Crosslinker μN/g |
|---|---|---|---|
| Comparative | 552 | 1.1 | 2.2 |
| Inventive 1 | 3570 | 6.9 | 13.8 |
| Inventive 2 | 1034 | 2 | 4 |

TABLE 5

|  | Capacitance μF | ESR mOhm | Yield % | DCL Fail % |
|---|---|---|---|---|
| Comparative | 13.4 | 95.5 | 10.9 | NA |
| Inventive 1 | 13.2 | 30.9 | 93.5 | 5 |
| Inventive 2 | 13.4 | 39.4 | 95.4 | 0 |

The content of crosslinker listed is normalized in terms of weight (μg), moles (μM), and normals (μN) per gram anode mass wherein the normals were determined based on the number of crosslinking sites per molecule. In Table 4, 1 μg is $10^{-6}$ grams, 1 μM is $10^{-6}$ moles and 1 μN is $10^{-6}$ Normals. For example, a crosslinking material with one crosslinking site would have one equivalent per molecule and molar content and normal content would be the same. A crosslinking material with two crosslinking sites would have two equivalents per molecule and molar content would be half of the normal content.

The analysis was performed on a liquid extractant using a capillary electrophoresis instrument (HP 3DCE model G1600AX) that employs dried crosslinker as a calibration standard. The liquid extractant sample was prepared by extracting polymer coated anodes using deionized water at 50° C. for 1 hour. Since this method calculates the content of anodes crosslinker based on the measured anionic portion of the crosslinker, the results are somewhat affected by anionic residue of anodes even when crosslinker is not applied, as shown in Inventive sample 1

Capacitance and ESR were measured at 120 Hz and 100K Hz, respectively. Leakage (DCL) failure was defined as leakage of greater than 100 μA at rated voltage at room temperature after 21 hrs in an atmosphere at 125° C. and 85% relative humidity. The tested capacitor was maintained at rated voltage throughout the test.

The invention has been described with reference to the preferred embodiments without limit thereto. One of skill in the art would realize additional embodiments and alterations which are not specifically stated but which are within the scope of the invention as set forth in the claims appended hereto.

What is claimed is:
1. A compound represented by Formula I wherein
$R^1$ and $R^2$ are independently selected from the group consisting of hydrogen, halo, alkyl having 1 or 2 carbon atoms, perfluoromethyl, alkoxy having 1 or 2 carbon atoms, perfluoromethoxy, hydroxy, and amino;

one of $R^3$ and $R^4$ is hydrogen, and the other is selected from the group consisting of hydroxy, alkoxy having 1 or 2 carbon atoms, nitro, alkyl having 1 or 2 carbon atoms, amino, halo, and cyano;

t is 0 or 1;

q is 0 or 1;

r is 0, 1, or 2;

X is C(O) and r is 0 and t is 0, or X is $N(R^{13})$ wherein $R^{13}$ is hydrogen or alkyl having from 1 to 3 carbon atoms;

one of $R^5$ and $R^6$ is hydrogen, and the other is selected from the group consisting of hydrogen, alkyl having 1 or 2 carbon atoms, hydroxy, alkoxy having 1 or 2 carbon atoms, fluoro, chloro, bromo, amino;

$R^7$ is y is 0, 1, 2, or 3;

m is 0, 1, 2, 3, or 4;

n is 0 or 1;

$R^8$ is hydrogen, methyl or ethyl and $R^9$ is hydrogen or methyl, or $R^8$ is hydroxy and $R^9$ is hydrogen, or $R^8$ is O and $R^9$ is absent, or $R^8$ and $R^9$ together are $CH_2CH_2$;

one of $R^{10}$ and $R^{11}$ is alkyl having from 1 to 3 carbon atoms, and the other is hydrogen or alkyl having from 1 to 3 carbon atoms;

$R^{12}$ is hydrogen or alkyl having from 1 to 3 carbon atoms, or when $R^{12}$ is hydrogen, a pharmaceutically acceptable salt of the compound.

2. The compound or salt of claim 1, wherein $R^1$ is methyl, $R^2$ is methyl, t is 0, q is 0, r is 1, $R^5$ is hydrogen or methyl, and $R^6$ is hydrogen.

3. The compound of claim 2, wherein $R^7$ is

4. The compound of claim 3, being 3-((3-(1H-tetrazol-5-yl)phenoxy)methyl)-2,4-dimethylphenol.

5. The compound or salt of claim 2, wherein $R^7$ is $R^8$ is hydrogen, $R^9$ is hydrogen, m is 1, and n is 0.

6. The compound or salt of claim 5, wherein the compound is selected from the group consisting of:

2-(3-(3-hydroxy-2,6-dimethylbenzyloxy)-4-methylphenyl)acetic acid;

2-(3-(3-methoxy-2,6-dimethylbenzyloxy)-4-methylphenyl)acetic acid; and 2-(3-(2,6-dimethyl-3-nitrobenzyloxy)phenyl)acetic acid.

7. A method of reducing the uric acid concentration in blood of, or increasing uric acid excretion from, a mammalian subject, comprising administering to the subject a compound or salt of claim 1 in an amount effective to reduce the uric acid concentration in blood of, or increase uric acid excretion from, the subject.

8. A method for treating in a subject a condition selected from the group consisting of gout, hyperuricemia, elevated levels of uric acid that do not meet the levels customarily justifying a diagnosis of hyperuricemia, renal dysfunction, kidney stones, cardiovascular disease, risk for developing cardiovascular disease, tumor-lysis syndrome, cognitive impairment, early-onset essential hypertension, and *Plasmodium falciparum*-induced inflammation, comprising administering to the subject a compound or salt of claim 1 in an amount effective to treat the condition.

9. The method of claim 7, wherein the subject is a human.

10. The method of claim 7, further comprising administering to the subject one or more other uric acid lowering drugs in a combined amount effective to reduce the uric acid concentration in blood of, or increase uric acid excretion from, the subject.

11. The method of claim 10, wherein the other uric acid lowering drug is selected from the group consisting of a xanthine oxidase inhibitor, a uricosuric agent, a urate transporter-1 inhibitor, a uricase, and a statin.

12. The method of claim 10, wherein the other uric acid lowering drug is administered in an amount that is less than the usual therapeutic dose when administered alone.

13. The method of claim 10, wherein the compound or salt and the one or more other uric acid lowering drugs are mixed together to form an admixture and the admixture is administered to the subject.

14. The method of claim 10, wherein the compound or salt and the one or more other uric acid lowering drugs are not mixed together to form an admixture but are administered independently to the subject.

15. The method of claim 10, wherein the compound or salt is formulated for oral administration.

16. The method of claim 7, wherein the compound is 3-((3-(1H-tetrazol-5-yl)phenoxy)methyl)-2,4-dimethylphenol.

17. The method of claim 7, wherein the compound is selected from the group consisting of:

2-(3-(3-hydroxy-2,6-dimethylbenzyloxy)-4-methylphenyl)acetic acid;

2-(3-(3-methoxy-2,6-dimethylbenzyloxy)-4-methylphenyl)acetic acid; and 2-(3-(2,6-dimethyl-3-nitrobenzyloxy)phenyl)acetic acid.

18. The method of claim 8, wherein the subject is a human.

19. The method of claim 8, wherein the compound is 3-((3-(1H-tetrazol-5-yl)phenoxy)methyl)-2,4-dimethylphenol.

20. The method of claim 8, wherein the compound is selected from the group consisting of:

2-(3-(3-hydroxy-2,6-dimethylbenzyloxy)-4-methylphenyl)acetic acid;

2-(3-(3-methoxy-2,6-dimethylbenzyloxy)-4-methylphenyl)acetic acid; and 2-(3-(2,6-dimethyl-3-nitrobenzyloxy)phenyl)acetic acid.

* * * * *